United States Patent [19]
Hörmansdörfer

[11] Patent Number: 5,997,578
[45] Date of Patent: *Dec. 7, 1999

[54] PROCESS FOR THE PRODUCTION OF A THREAD HAVING A VARIABLY MODIFIABLE THREAD PROFILE AND PREFERRED APPLICATION OF THE PROCESS

[76] Inventor: Gerd Hörmansdörfer, Kastanieneck 6A, D-3103 Burgdorf, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/513,818
[22] PCT Filed: Dec. 28, 1994
[86] PCT No.: PCT/DE94/01551
 § 371 Date: Sep. 5, 1996
 § 102(e) Date: Sep. 5, 1996
[87] PCT Pub. No.: WO95/18586
 PCT Pub. Date: Jul. 13, 1995

[30] Foreign Application Priority Data
 Jan. 2, 1994 [DE] Germany .................. 44 00 001

[51] Int. Cl.⁶ ..................................... A61F 2/32
[52] U.S. Cl. ........................................... 623/22
[58] Field of Search .................. 623/22, 23; 411/412

[56] References Cited

U.S. PATENT DOCUMENTS

| | | | |
|---|---|---|---|
| 4,822,367 | 4/1989 | Stuhmer | 623/22 |
| 5,336,015 | 8/1994 | Stewart | 411/412 |
| 5,358,533 | 10/1994 | Noiles | 623/23 |

FOREIGN PATENT DOCUMENTS

| | | | |
|---|---|---|---|
| 2172950 | 10/1986 | United Kingdom | 411/311 |

*Primary Examiner*—Michael J. Milano
*Attorney, Agent, or Firm*—Pendorf & Cutliff

[57] ABSTRACT

A process for producing threads by metal cutting when a more or less gradual change of the thread profile is desired in at least one of its sections. When producing a thread by turning, by milling or by turning and milling, the thread is cut in at least two successive operations with at least two different thread pitches and/or an offset value or a continuously changing pitch. The process is preferred for making possible a gradual change in the height and shape of the teeth or, as the case may be, the design of the thread bottom of a self-cutting thread to be progressively adapted to the curved outer profile of an artificial hip-joint socket.

26 Claims, 2 Drawing Sheets

PROCESS FOR THE PRODUCTION OF A THREAD HAVING A VARIABLY MODIFIABLE THREAD PROFILE AND PREFERRED APPLICATION OF THE PROCESS

BACKGROUND OF THE INVENTION

1. Field of the Invention

The invention relates to a special process for the cutting production of threads, in which, at least in a part region of their extension, a more or less sliding influence on or correction of the thread profile is desired. Such a design can be advantageous for specific uses. Such a preferred use of the process is proposed.

2. Description of the Related Art

Threads are in widespread use as constructive elements in general mechanical engineering. Threads are usually made cylindrical, and in addition conical threads are also commonly used, for example for oil-field pipes. A large number of different thread profiles are known and are laid down in standards. The said profile on a workpiece is usually invariable, that is to say the thread profile at the thread start is identical to that at the thread end. Exceptions are conceivable, however, in which it could be advantageous to have a shape of the thread profile formed from thread groove and thread tooth which changes in a flowing manner at least in a part region of the thread, for example in order to make it easier to introduce a screw thread into a nut thread.

However, special geometrical conditions with respect to the thread prevail primarily in threads on curved surfaces, such as occur particularly in the case of screw-in artificial hip-joint sockets. Here, with regard to the outer shape of the shell body, for example hypospherical, hemispherical or hyperspherical, conico-spherical, parabolic, toroidal, elliptic or similar geometries are known. Metal-cutting production processes for the threads of screw sockets of this type result, sometimes necessarily, in distortions of the thread profile which vary in flowing manner and which in most cases are neither intended nor desired. Particularly the use of thread teeth having asymmetric flank angles, there is the phenomenon that, depending on the tilting direction of the resulting thread tooth, the tooth height from the socket equator towards the socket pole increases or decreases in a flowing manner, the result of this then being either much too large or virtually stunted thread teeth at the near-pole thread start. In the first case, extremely large thread teeth led to the fact that very high forces become necessary in order to screw in the socket or the implant cannot be screwed in until there is full bone contact. In the second case, only very feeble primary fixation is to be achieved. In both cases, there is the risk that the implant will work loose, and this would mean a further operation on the patient as a consequence.

SUMMARY OF THE INVENTION

The object was, therefore, to provide a hip-joint socket which can be produced by metal cutting and with a thread located on the curved outer surface and having asymmetric flank angles of the said tooth and a thread-tooth height adaptable along the thread extension, as well as a process for the production of such a special thread for this and other uses.

The object is achieved, according to the invention, in that the thread groove of a thread located on a curved outer surface is divided into at least two strip-like part surfaces of different pitch, whereas the width of the thread bottom, as measured in the radial projection, changes in a flowing manner along the extension of the thread, in such a way that the thread-tooth height which results in each case is adapted to the constructive preconditions. Furthermore, the invention makes available a process for the production of such a special thread.

Thus, it is proposed to machine the said groove along the same contour, in the region provided for the adaptation of the thread profile, at least in two production passes with at least two different pitches. For this purpose, the same tool or two or more different tools can optionally be used. If only one tool is to be employed, its two flanks must correspond to the shape of the two thread flanks. The invention here affords the possibility of choosing to use either a tool which corresponds in its profile to the profile of the thread groove at its narrowest point or a tool which is generally narrower than the thread groove. In the second case, it is proposed, for the cutting of the thread, to include additionally an appropriately adapted offset value besides the use of at least two different pitches for the machining passes, in order to compensate the difference between tool width and thread-groove width. This procedure is particularly advantageous because, for example, a smaller tip rounding of the machining tool thereby becomes possible. As a result, the thread bottom can have a finer definition and be adapted more closely to the curved outer surface desired.

Furthermore, the invention offers the possibility of choosing to carry out the thread machining by means of more than two production passes or by means of two or more tools. If, for example, three production passes are employed, it is recommended to machine essentially one side of the thread groove in one of the production passes, essentially the other side of the thread groove in a further production pass and essentially the groove bottom in a third production pass. At the same time, the maximum or minimum value of the pitch is used for the tools cutting the sides of the thread groove and the respective flanks of the thread teeth, whilst it is proposed to use a pitch located between these two values for the tool cutting essentially the middle of the thread bottom. With an increasing number of machining passes or tools, it is thus possible, with a correspondingly small rounding of the respective tool tip, to avoid an unfavourably coarse rounding of the thread-tooth root and to achieve an even better adaptation of the thread bottom to the desired contour.

The process according to the invention can be used on various machines by means of different cutting techniques, for example by means of lathe-turning, milling and turning or milling. In the lathe-turning of the threads, it is customary to machine the thread groove in a plurality of passes by means of a lathe chisel. The production pass is then designated as a thread-cutting cycle. In the case of a single run, only a little material is removed, but, for this purpose, the work can be carried out at high feed speeds. In contrast, in thread-milling, a production pass can consist of a single run, for which, however, as a rule an expenditure of time somewhat greater in comparison with lathe-turning occurs as a result of the low feed speed required. For cutting the thread according to the invention, modern computer-controlled machines, so-called CNC machines, are necessary. The path to be described by the respective tool in relation to the workpiece must be entered in the corresponding CNC program. Furthermore, the different pitch to be taken into account during cutting for the respective production pass is to be specified in the program. For synchronizing the production passes or tools, it is necessary to compute exactly the different starting points for the individual production passes or cutting cycles.

The computation of two such starting points will be explained by means of an example of lathe production. A thread to be cut on a curved outer surface is to extend from $z_3=-8$ to $z_4=-27$. A pitch $s_1$ of 4 mm to be covered is assumed for a tool A. In view of the necessary synchronization distance (usually 2 times thread pitch) of 8 mm, the starting point for the thread-cutting cycle is set at $z_2=0$, whilst the end point remains at $z_4=-27$. A travel in z of 27 mm is thus obtained. To achieve a specific flowing adaptation of the thread-tooth height, for a second tool B the pitch $s_2$ to be taken into account was set at 4.2 mm. At the point $z_4=-27$, the two tools are to be synchronous. The starting point $z_1$ for the tool B is then calculated as follows:

$$z_1 = \frac{[z_2 - z_4] \cdot s_2}{s_1} + z_4$$

$$z_1 = \frac{[0 - (-27)] \cdot 4.2}{4} + (-27)$$

$$z_1 = +1.35$$

If an offset value is used for the axial parallel shift of a single tool or if a position of two tools is not congruent at any point of the thread, this offset value is to be added or subtracted with the z value, determined according to the above formula, for the starting point.

It is proposed, as particularly advantageous, to combine the process, explained in more detail above, for the production of a thread having a variably modified thread profile with a process, on which the applicant has already applied for a patent, for adapting the thread bottom to curved surfaces. The said application (European Patent Application 91250274.7, Publication No. 0,480,551 A1) presents a process, by means of which the thread bottom can be adapted virtually perfectly to a curved shape, in that cutting tools having end angles differing in relation to the thread bottom are used for production. These are moved on different paths, but with the same pitch relative to the workpiece. In the case of different (asymmetric) tooth-flank angles, the tooth heights of threads of this type, the said tooth heights then normally changing in a flowing manner, can be corrected to the desired values by additionally moving the individual tools with different pitches relative to the workpiece.

In a special version of the process hereby proposed, one or more tools run successively off the thread groove of a screw-in hip-joint socket of this type by the use of an offset and of different pitches, in such a way that, in the middle of the thread bottom between the thread teeth of conventional depth (for example, a depth of between 2.5 and 3.5 mm), a further very small thread tooth (for example, with a depth of between 0.2 and 1.5 mm, preferably between 0.3 and 1.0 mm) is formed. This type of machining serves for providing a micro/macro thread on the outer surface of the screw socket, the macroteeth of normal size serving essentially for primary fixation and the small microteeth serving essentially for surface enlargement and therefore for secondary fixation. By setting the geometrical cutting conditions from the number of machining runs and their respective offset values or pitch values, it is possible, for such a micro/macro thread, to determine how far the tooth heights of both the macroteeth and the microteeth are either to be maintained or to be varied in a flowing manner over the contour. The proposed micro/macro thread achieves a highly reliable anchoring of the implant in the bone structure, because the advantage of a larger thread pitch and of the resulting broader width and high load-bearing capacity of the bone structure located in the thread grooves is thereby associated in a beneficial way with the advantage of surface enlargement and the accompanying reduction in the specific interfacial stress between the implant and bone structure.

BRIEF DESCRIPTION OF THE DRAWINGS

For a fuller understanding of the nature and objects of the present invention reference should be made by the following detailed description taken in with the accompanying drawings in which.

DETAILED DESCRIPTION OF THE INVENTION

For a better understanding, the invention will be explained in more detail below with reference to the four drawing figures.

Figure 1:
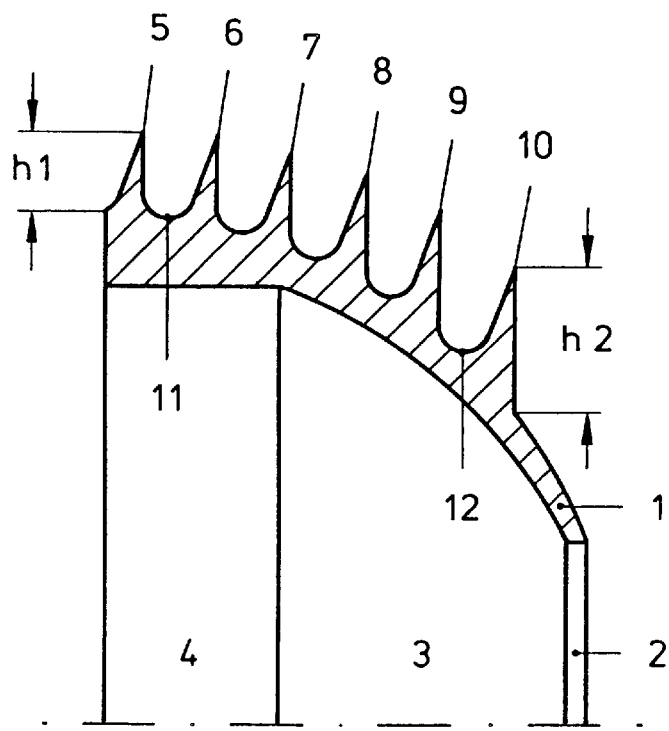
FIG. 1 shows a sectional and half-side representation of a somewhat exemplary embodiment of an artificial hemispherical hip-joint socket with a conventionally produced screw thread.

FIG. 1 shows a sectional and half-side representation of a somewhat simplified exemplary embodiment of an artificial hemispherical hip-joint socket of medium size with a conventionally produced screw thread on a scale of approximately 2.5:1. In this, a value of 4 mm was chosen for the thread pitch. The thread teeth have been shown slightly exaggerated, so that the details can be made more clearly visible. The hip-joint socket (1) is provided with a bottom hole (2). Its inner contour is divided into a spherical portion (3) and a cylindrical region (4). The six thread teeth (5, 6, 7, 8, 9 and 10) have an asymmetric profile. Their flank facing the pole of the socket has an angle of 0°, and their flank facing the equator of the socket has an angle of 20°. This results in a tilting angle of the thread teeth of 10° in the direction of the socket pole. This tilting direction of the thread teeth appears particularly beneficial for the intended use in a hip-joint socket, because, in view of the predetermined load direction, better conditions for the introduction of force into the human pelvis can thereby be achieved. Since the thread was cut in the conventional way with only one tool and with a constant pitch, the thread bottom (11) near the equator is identical to the thread bottom (12) near the pole. The tilting angle of the thread teeth and the production process used for the thread result in a flowing variation in the thread-tooth height. It can be seen clearly that the radially measured thread-tooth height h 2 near the pole is approximately twice as large as the thread-tooth height h 1 near the equator. Although flowing increases or decreases in the thread-tooth height may be perfectly desirable to a particular degree, especially in hip-joint sockets, and various arguments for this are also put forward in the field, nevertheless such a pronounced enlargement of the thread-tooth height is extremely disadvantageous, because this involves action unnecessarily deep into the bone material. Furthermore, particularly in the case of self-cutting screw sockets, thread teeth of such size at the near-pole thread start lead to very high screw-in forces, since, in the region of the abrupt increase in the thread-tooth height at the thread start, the cutting work during the screwing into the pelvis is distributed over only a few cutting edges. The introduction of the hip-joint socket thereby may be impaired before full bone contact is achieved.

Figure 2:
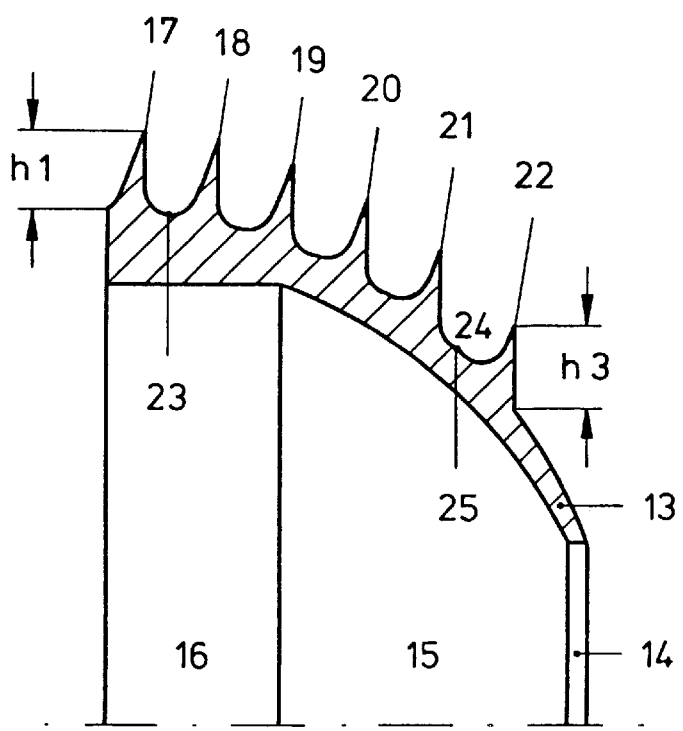
FIG. 2 shows, in a mode of representation identical to FIG. 1, the simplified and slightly exaggerated exemplary embodiment of an artificial hemispherical hip-joint socket with a screw thread produced in accordance with the invention.

FIG. 2 shows, in a mode of representation identical to that of FIG. 1, the simplified and slightly distorted exemplary embodiment of a hip-joint socket according to the invention with a screw thread. The hip-joint socket (13) shown corresponds to that of FIG. 1 in its bottom hole (14), its inner contour consisting of a spherical portion (15) and of the cylindrical region (16) and the number of its thread teeth. Both the near-equator thread tooth (17) with its shape and the amount of its depth h 1 and the thread bottom (23) of the adjacent thread groove are identical respectively to the corresponding thread tooth (5) and to the adjacent thread bottom (11) of FIG. 1. As a result of the thread machining according to the invention by means of two production passes with a different pitch, the thread-tooth flank drawn at 0° being cut, as before, with a pitch of 4 mm, but, in contrast to this, the thread flank drawn at 20° being cut with a pitch of approximately 4.16 mm, a radially measured tooth height h 3 corresponding to the tooth height h 1 of the near-equator tooth (17) is now produced for the near-pole thread tooth (22). It is also clear that the thread bottom of the near-pole thread groove (24) is now altogether wider than the near-equator thread bottom (23) and has assumed a shape diverging from this and coming closer to the spherical outer surface of the socket shell. A slightly eccentric edge (25) is indicated faintly in the thread bottom of the near-pole thread groove (24), the said edge (25) extending along the thread groove by virtue of the machining mode according to the invention and slowly thinning in its developed trend in the direction of the socket equator. The maximum height of this elevation is dependent on the geometry or rounding of the tool bit used and therefore, by appropriate selection, can be adapted to the constructive preconditions for the design of the thread bottom.

Figure 3:
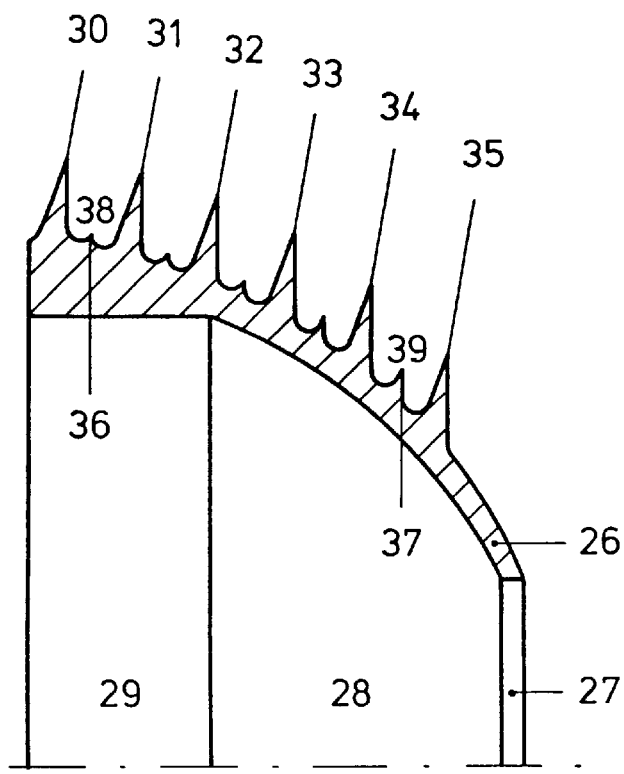
FIG. 3 shows, in a mode of representation identical to FIG. 1, an artificial paraspherical hip-joint socket with a micro/macro screw thread produced in accordance with the invention.

The example of a special version of the process according to the invention is represented in FIG. 3 in the form of a paraspherical screw socket having a micro/macro thread. In the way already known from the preceding figures, the drawing figure shows a sectional diagram of a screw socket (26) with bottom hole (27), the interior of which is formed from a spherical portion (28) with an adjoining cylindrical region (29). The screw socket is equipped on its outer surface with a macro thread, from which six teeth (30, 31, 32, 33, 34, 35) are obtained in the sectional diagram. In contrast to the shape of the sphere, in the exemplary embodiment shown a para-spherical contour is produced by means of the thread bottom and, primarily in the region after the near-pole thread start, has been provided with a certain contraction in relation to a spherical outer surface, in order to provide room here for the bone chips occurring when the socket is screwed into the bony bed. In the thread groove (38) near the socket edge, a not very tall tooth (36) of the microthread extending round approximately centrally in the thread groove can be seen. In the near-pole thread groove (39), the tooth (37) of the microthread has increased in height. The greater increase in height of the microtooth when the radial height of the macrotooth increases only slightly results from machining by means of a single tool, two different pitches and a reciprocal offset value being used in two machining runs. The process affords, in general, the possibility of increasing or adapting the number of machining passes of different pitch and/or reciprocal offset values or the pitch differences themselves, in order to influence the geometrical cutting result. Consequently, for example, the microthread can be set without further action to a constant tooth height.

Figure 4:
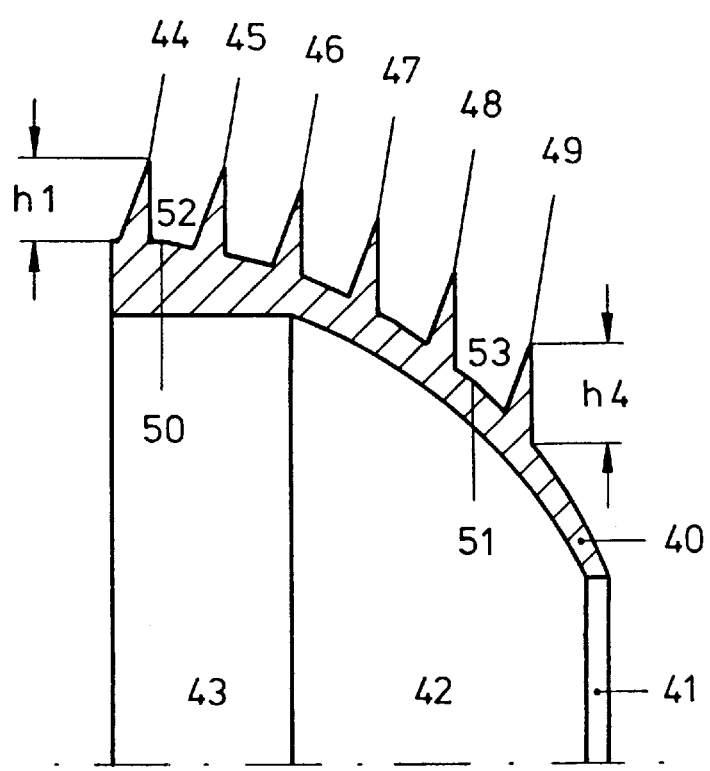
FIG. 4 shows an artificial hemispherical hip-joint socket wherein the near-perfect spherical outer surface is produced using five different cutting tools in accordance with the invention.

The exemplary embodiment shown in FIG. 4 also corresponds in the chosen form of representation to the figures shown previously. This relates to a hemispherical screw socket (40), the spherical outer surface of which was reproduced virtually perfectly by employing a thread-producing process known from European Patent Application 91250274.7 by means of the use of five different cutting tools having the individual front-edge angles of 2°, 14°, 25°, 35° and 44°. Both in the thread groove (52) located near the socket edge and in the near-pole thread groove (53), the desired curved contour is reproduced exactly in such a way that the ridges (50) and (51) necessarily occurring as a result of the process are scarcely visible. For the exemplary embodiment shown, the said process was combined with the process on which a patent is hereby applied for, in order to influence the height of the thread teeth inclined at 10° in the pole direction. At the same time, the respective pitches for the five different cutting tools were selected so that the tool cutting the near-pole thread flank was operated with the smallest pitch and the tool cutting the thread flank pointing to the socket edge was operated with the largest pitch. The pitch difference between the smallest and largest pitch was set so that the radially measured thread-tooth height h 1 of the thread tooth (44) rises to a slightly increased value h 4 over the thread teeth (45, 46, 47, 48) as far as the thread tooth (49), this rise in turn resulting from the fact that an attempt was made to bring the thread-tooth flank cut at an angle of 20° to an approximately uniform length. The screw socket with its bottom hole (41) and with its inner contour composed of the spherical portion (42) and of the cylinder (43) otherwise corresponds to the exemplary embodiments shown previously.

It can be seen from the last exemplary embodiment that the process according to the invention is not restricted to producing a uniform thread-tooth height over the entire range of extension of the thread. On the contrary, it affords numerous possibilities of variation, in that either exactly determinable increases or decreases in the thread-tooth heights can be brought about by an appropriate setting of the different thread pitches used or these modifications can be introduced partially in part regions of the thread extension or in a sliding manner by means of the programming of a continuously changing pitch. Consequently, the invention makes available a means of highly flexible use for the optimum adaptability of special threads, particularly of curved special threads.

What is claimed is:

1. Process for the cutting production of a thread profile on a body, said thread profile having a first thread flank, a second thread flank, and a thread bottom between said flanks, said thread profile gradually changing over at least a portion of said body, wherein said gradually changing thread profile is produced by a process comprising:

machining said first thread tooth flank of said thread profile with at least one machining pass with a machining tool set at a first pitch; and machining said second thread tooth flank of said thread profile with at least one machining pass with a machining tool set at a second pitch, wherein said first pitch differs from said second pitch.

2. Process as in claim 1, wherein said machining tool for machining said first tooth flank is a different tool from the tool for machining said second tooth flank.

3. Process as in claim 2, comprising machining a part of the thread bottom between the thread flanks with a third machining tool, wherein the pitch used for said third machining tool is between the pitch used for the first machining tool and the pitch used for the second machining tool.

4. Process for the cutting production of a thread profile as in claim 1, wherein said process comprises:
    machining said first thread tooth flank of said thread profile with at least a first machining pass with a machining tool and at least a second machining pass offset from said first machining pass; and
    machining said second thread tooth flank of said thread profile with at least a first machining pass with a machining tool and at least a second machining pass offset from said first machining pass.

5. Process for the cutting production of a thread profile as in claim 4, wherein said machining tool for machining said first thread tooth flank is a different tool from the tool for machining said second tooth flank.

6. Process as in claim 1 comprising:
    machining said first thread tooth flank of said thread profile at a first pitch with at least a first machining pass with a machining tool and at least a second machining pass offset from said first machining pass; and
    machining said second tooth flank of said thread profile at a second pitch with at least a first machining pass with a machining tool and at least a second machining pass offset from said first machining pass.

7. Process as in claim 6, wherein said machining tool for machining said first tooth flank is a different tool from the tool for machining said second tooth flank.

8. Process as in claim 1, comprising:
    machining said first thread tooth flank of said thread profile at a first pitch with at least a first machining pass with a machining tool and at least a second machining pass offset from said first machining pass; and
    machining said second tooth flank of said thread profile at a second pitch with at least a first machining pass with a machining tool and at least a second machining pass offset from said first machining pass,
    wherein the starting point for said machining of said second tooth flank is offset from the starting point for machining of said first tooth flank.

9. Process for the cutting production of a thread profile as in claim 8, wherein said machining tool for machining said first thread tooth flank is a different tool from the tool for machining said second tooth flank.

10. Process according to claim 8, wherein the starting point of one of the machining passes is used as the reference point to which the offset value(s) of the other machining p asses are added or subtracted.

11. Process as in claim 1, wherein the starting point for said machining of said second thread tooth flank is offset from the starting point for machining of said first thread tooth flank.

12. Process for the cutting production of a thread profile on a body, said thread profile having a first thread flank, a second thread flank, and a thread bottom between said flanks, said thread profile gradually changing over at least a portion of said body, wherein said gradually changing thread profile is produced by a process comprising:
    machining said first thread tooth flank of said thread profile with at least one machining pass with a machining tool; and
    machining said second thread tooth flank of said thread profile with at least one machining pass with a machining tool set at a second pitch, wherein the starting point for said machining of said second thread tooth flank in relation to the starting point for machining of said first thread tooth flank is offset and dependent upon the equation:

$$Z_1 = \frac{(Z_2 - Z_4) \cdot S_2}{S_1} + Z_4$$

where
$Z_1$=tool starting point for machining said second thread tooth flank
$Z_2$=tool starting point for machining said first thread tooth flank
$Z_4$=convergent tool point of both machining passes
$S_1$=first thread pitch
$S_2$=second thread pitch.

13. Process as in claim 1, wherein said machining tool for machining said first tooth flank is a different tool from the tool for machining said second tooth flank.

14. Process for the cutting production of a thread profile on a body, said thread profile having a first thread flank, a second thread flank, and a thread bottom between said flanks, said thread profile gradually changing over at least a portion of said body, wherein said gradually changing thread profile is produced by a process comprising:
    machining said first thread tooth flank of said thread profile with at least a first machining pass with a machining tool and at least a second machining pass offset from said first machining pass at a first pitch; and
    machining said second thread tooth flank of said thread profile with at least a first machining pass with a machining tool and at least a second machining pass offset from said first machining pass at a second pitch, wherein the starting point for said machining of said second thread tooth flank in relation to the starting point for machining of said first thread tooth flank is offset and dependent upon the equation:

$$Z_1 = \frac{(Z_2 - Z_4) \cdot S_2}{S_1} + Z_4$$

where
$Z_1$=tool starting point for machining said second thread tooth flank
$Z_2$=tool starting point for machining said first thread tooth flank
$Z_4$=convergent tool point of both machining passes
$S_1$=first thread pitch
$S_2$=second thread pitch.

15. Process for the cutting production of a thread profile as in claim 14, wherein said machining tool for machining said first thread tooth flank is a different tool from the tool for machining said second tooth flank.

16. Process for the cutting production of a thread profile on a body, said thread profile having a first thread flank, a second thread flank, and a thread bottom between said flanks, said thread profile gradually changing over at least a portion of said body, wherein said gradually changing thread profile is produced by a process comprising:
    machining said first thread tooth flank of said thread profile with at least one machining pass with a machining tool; and
    machining said second thread tooth flank of said thread profile with at least one machining pass with a machining tool, wherein said thread bottom describes a curved outer surface on said body, wherein said thread profile is machined on different paths by means of different cutting tools having frontal cutting angles differing in relation to each other, and wherein different pitches for said cutting tools are used during the machining passes.

17. Process for the cutting production of a thread profile on a body, said thread profile having a first thread flank, a second thread flank, and a thread bottom between said flanks, said thread profile gradually changing over at least a portion of said body, wherein said gradually changing thread profile is produced by a process comprising:

machining said first thread tooth flank of said thread profile with at least one machining sass with a machining tool. and machining said second thread tooth flank of said thread profile with at least one machining pass with a machining tool, wherein said body is a hip-joint socket having a curved outer contour including a socket rim and a socket pole, wherein said first thread flank faces said socket pole and said second thread flank faces said socket rim, and wherein a smaller pitch is used for the machining passes of the tool which cuts the first thread flank than is used for the machining passes of the tool which cuts the second thread flank.

18. Process as in claim 17, wherein said curved outer contour is selected from the group consisting of conicospherical, hypersperical, hemispherical, hypospherical, paraspherical, parabolical, elliptical, and toroidicol.

19. A screw-in hip-joint socket having a curved outer contour provided with a self-tapping thread for cement-less anchoring in the acetabulum by rotating about an axis, said thread having a profile comprising a first thread flank, a second thread flank, and a thread bottom between said flanks, said thread profile gradually changing over at least a portion of said self-tapping thread, wherein said gradually changing thread profile is produced by a process comprising:

machining said first thread tooth flank of said thread profile with at least one machining pass with a machining tool; and machining said second thread tooth flank of said thread profile with at least one machining pass with a machining tool in such a way that the thread bottom is divided into at least two strip-like part surfaces of different pitch.

20. Threaded hip-joint socket according to claim 19, wherein the width of the thread bottom as measured in the axial direction changes gradually along the extension of the thread from the socket pole towards the socket rim.

21. Threaded hip-joint socket according to claim 19, wherein said thread bottom describes a curved outer surface on said body, wherein said thread profile is machined on different paths by means of different cutting tools having frontal cutting angles differing in relation to each other, and wherein different pitches of cutting tools are used during the machining passes.

22. Threaded hip-joint socket according to claim 19, wherein said micro-thread tooth is at least 50% smaller than said self-tapping thread teeth.

23. Screw-in hip-joint socket having a curved outer contour provided with a self-tapping thread for cement-less anchoring in the acetabulum by rotating about an axis, said thread having a profile comprising a first thread flank, a second thread flank, and a thread bottom between said flanks, said thread profile gradually changing over at least a portion of said self-tapping thread, wherein said gradually changing thread profile is produced by a process comprising:

machining said first thread tooth flank of said thread profile with at least one machining pass with a machining tool; and machining said second thread tooth flank of said thread profile with at least one machining pass with a machining tool in such a way that the thread bottom is divided into at least two strip-like part surfaces of different pitch, further comprising a micro-thread tooth in the thread bottom formed between two self-tapping thread teeth, wherein said micro-thread tooth is smaller in height than said self-tapping thread teeth.

24. Threaded hip-joint socket having a curved outer contour having a pole, a rim, a self-tapping thread for cement-less anchoring in the acetabulum, said thread having a profile comprising a first thread flank, a second thread flank, and a thread bottom between said flanks, said thread bottom comprising strip-like part surfaces generally defining the curved outer contour of the hip-joint socket shell, said strips provided angularly in steps and extending parallel to one another and obliquely relative to the development of the thread bottom, the thread tooth being inclined towards the pole of the hip-joint socket, wherein the axial width of the thread bottom, as measured in the radial projection, varies gradually along the thread from the socket pole towards the socket rim, and wherein the strip-like part surface of the thread bottom extending along the thread-tooth flank facing the socket pole has a smaller pitch than the strip-like part surface of the thread bottom extending along the thread-tooth flank facing the socket rim.

25. A threaded hip-joint socket provided with a self-tapping thread for cement-less anchoring in the acetabulum, said thread having a profile comprising a first thread tooth flank, a second thread tooth flank, a thread bottom between said flanks, said thread bottom representing a curved outer contour of the socket body, said thread profile gradually changing over at least a portion of said body, wherein at least a portion of the thread is machined using a continuously changing pitch.

26. Process for the cutting production of a thread profile on a body, said thread profile having a first thread flank, a second thread flank, a thread bottom between said flanks, said thread profile gradually changing over at least a portion of said body, wherein said gradually changing thread profile is produced by a process comprising:

machining said first thread tooth flank of said thread profile with at least a first machining pass with a machining tool and at least a second machining pass offset from said first machining pass; and machining said second thread tooth flank of said thread profile with at least a first machining pass with a machining tool and at least a second machining pass offset from said first machining pass, wherein said machining tool for machining said first thread tooth flank is a different tool from the tool for machining said second tooth flank, wherein the cutting tool has a rounded tip; and wherein the cutting tool rounded tip is smaller than the thread-groove width, wherein the starting point for said machining of said second thread tooth flank in relation to the starting point for machining of said first thread tooth flank is offset and dependent upon the equation:

$$Z_1 = \frac{(Z_2 - Z_4) \cdot S_2}{S_1} + Z_4$$

where $Z_1$=tool starting point for machining said second thread tooth flank $Z_2$=tool starting point for machining said first thread tooth flank $Z_4$=convergent tool point of both machining passes $S_1$=first thread pitch $S2$ =second thread pitch.

* * * * *

UNITED STATES PATENT AND TRADEMARK OFFICE
CERTIFICATE OF CORRECTION

PATENT NO. : 5,997,578
DATED : December 7, 1999
INVENTOR(S) : Gerd Hörmansdörfer It is certified that error appears in the above-identified patent and that said Letters Patent is hereby corrected as shown below:

Title page,
[76] Inventor: Gerd Hörmansdörfer, Kastanieneck 6A, D-31303, Burgdorf, Germany Column 9,
Line 59, cancel beginning with "22. Threaded" to and including "thread teeth."
Line 61, and insert the following claim:

22. Screw-in hip-joint socket having a curved outer contour provided with a self-tapping thread for cement-less anchoring in the acetabulum by rotating about an axis, said thread having a profile comprising a first thread flank, a second thread flank, and a thread bottom between said flanks, said thread profile gradually changing over at least a portion of said self-tapping thread, wherein said gradually changing thread profile is produced by a process comprising:

machining said first thread tooth flank of said thread profile with at least one machining pass with a machining tool; and machining said second thread tooth flank of said thread profile with at least one machining pass with a machining tool in such a way that the thread bottom is divided into at least two strip-like part surfaces of different pitch, further comprising a micro-thread tooth in the thread bottom formed between two self-tapping thread teeth, wherein said micro-thread tooth is smaller in height than said self-tapping thread teeth.

Line 62, cancel beginning with "23. Screw-in" to and including "thread teeth."

UNITED STATES PATENT AND TRADEMARK OFFICE
CERTIFICATE OF CORRECTION

PATENT NO. : 5,997,578
DATED : December 7, 1999
INVENTOR(S) : Gerd Hörmansdörfer It is certified that error appears in the above-identified patent and that said Letters Patent is hereby corrected as shown below:

<u>Column 10,</u>
Line 13, and insert the following claim:
    23. Threaded hip-joint socket according to Claim 22, wherein said micro-thread tooth is at least 50% smaller than said self-tapping thread teeth.

Signed and Sealed this

Ninth Day of October, 2001

*Attest:*

*Nicholas P. Godici*

NICHOLAS P. GODICI
*Attesting Officer    Acting Director of the United States Patent and Trademark Office*